(12) United States Patent
Nagashima et al.

(10) Patent No.: US 6,514,705 B2
(45) Date of Patent: Feb. 4, 2003

(54) METHOD FOR ANALYZING PHYLETIC LINEAGE OF SCALLOP

(75) Inventors: Koji Nagashima, Hokkaido (JP); Maremi Sato, Hokkaido (JP)

(73) Assignee: Hokkaido Federation of Fisheries Cooperative Associations (JP)

( * ) Notice: Subject to any disclaimer, the term of this patent is extended or adjusted under 35 U.S.C. 154(b) by 0 days.

(21) Appl. No.: 09/802,936

(22) Filed: Mar. 12, 2001

(65) Prior Publication Data

US 2002/0081593 A1 Jun. 27, 2002

(30) Foreign Application Priority Data

May 16, 2000 (JP) ........................................ 2000-148570

(51) Int. Cl.[7] ........................... C07H 21/04; C12Q 1/68; C12P 19/34
(52) U.S. Cl. ....................... 435/6; 435/91.1; 435/91.2; 536/23.1; 536/24.3
(58) Field of Search .................... 435/6, 91.1, 91.2; 536/23.1, 24.3

(56) References Cited

PUBLICATIONS

Berschick (Biotechniques (1997): 23(3) 494–498).*
Canapa et al. (J. Mol. Evol. (Jan. 2000) 50(1): 93–97).*
Boulding et al. (Can J. Aquar. Sci. (1993) 50(6): 1147–1157).*

* cited by examiner

*Primary Examiner*—Kenneth R. Horlick
*Assistant Examiner*—Alexander H. Spiegler
(74) *Attorney, Agent, or Firm*—Browdy and Neimark, PLLC

(57) ABSTRACT

Method for analyzing a phyletic lineage of scallop, which comprises the steps of sequencing a mitochondrial DNA of the scallop to determine a nucleotide base sequence of the mitochondrial DNA, wherein the nucleotide base sequence includes a non-coding region containing a nucleotide base substitution locus which shows a sequence polymorphism indicative of a particular lineage of the scallop. Mitochondrial DNA of the scallop is amplified by PCR, using a suitable primer set designed on the basis of nucleotide base sequences conserved among known shellfish mitochondrial 16S rRNA and 12S rRNA genes, followed by sequencing to determine a non-coding region therein. In such non-coding region, a nucleotide base substitution locus is located, whereby a particular lineage of the scallop is determined. Based on those steps, a Japanese scallop, *Patinopecten yessoensis*, is analyzed as to the nucleotide base sequence and lineage thereof.

11 Claims, 5 Drawing Sheets

FIG. 1

| Primer name | Sequence 5' - 3' |
|---|---|
| Pyso 16S AF | GCACCTTTGCATCATGGCTTAT |
| Pyso 16S AR | ATAAGCCATGATGCAAAAGCTGC |
| Pyso 16S BF | CGGCGAAGCCAGTCAGTTTCTATC |
| Pyso 16S BR | AAACTGACCTGGCTTACGCCGGTCTG |
| Pyso 12S AF | TCCAACCAGTGCCAGCAGT |
| Pyso 12S AR | ACTGCTGGCACCTGGTTGGA |
| Pyso 12S BF | GTGTACACATCGCCCGTCGCTCT |
| Pyso 12S BR | AGAGCGACGGGCGATGTGTACAC |
| Pyso NcF | GGTAGTTTGGTTCTGGTTACCT |
| Pyso NcR | AGGTAACCAGAACCAAACTACC |

FIG. 2

| Populations Haplotypes | Nucleotide base substitution loci | | | | | | | | | | | | | | | | Number of Individual(s) | Population frequency(%) | Nucleotide base diversity* |
|---|---|---|---|---|---|---|---|---|---|---|---|---|---|---|---|---|---|---|---|
| | 126 | 269 | 285 | 300 | 301 | 302 | 308 | 345 | 346 | 350 | 368 | 378 | | | | | | | |
| SAROMA Gs-1 | A | T | C | C | - | T | C | C | T | T | A | G | | | | | 6 | 31.58 | 0.80 |
| Gs-2 | | | | | | | | | | | C | G | | | | | 3 | 15.79 | |
| Gs-3 | | W | | | | | | | | | C | R | | | | | 1 | 5.2 | |
| Gs-4 | | | | | - | | C | | | | | | | | | | 2 | 10.53 | |
| Gs-5 | | | | | - | | C | | | T | | | | | | | 1 | 5.2 | |
| Gs-6 | | | | | - | | | T | | | | | | | | | 1 | 5.2 | |
| Gs-7 | | | | | - | | | | A | | | | | | | | 1 | 5.2 | |
| Gs-8 | | | | | - | | | | | | | | | | | A | 2 | 10.53 | |
| Gs-9 | G | | | | - | | | | | | | | | | | A | 1 | 5.2 | |
| Gs-10 | | | G | | - | | | | | | | | | | | A | 1 | 5.2 | |
| AOMORI Ga-1 | A | T | C | C | - | T | C | C | T | T | A | G | | | | | 3 | 15.0 | 0.38 |
| Ga-2 | | | G | | - | | | | | | | | | | | | 1 | 5.0 | |
| Ga-3 | | | G | | - | | | | | | | | | | | | 2 | 10.0 | |
| Ga-4 | | | | | - | | | | | | | | | | | A | 13 | 65.0 | |
| Ga-5 | | | | | - | | | | | | | | | | | A | 1 | 5.0 | |

*Total compared bases are 221 bases

Lane 1: SAROMA sample (Primer set used: Pyso 16S BF and Pyso 12S BR)
Lane 2: AOMORI sample (Primer set used: same as above)
Lane 3: U.S. sample (Primer set used: Pyso 12S BF and Pyso 16S BR)
M: Maker (500bp Ladder)

FIG. 4(B)1

```
GAAGCCAGGT  CAGTTTCTAT  CTTCTTTCAT  TAAAATTTAG  GCGGTAGGGT
            Pyso 16SBF→                                   100
ACGAAAGGAC  ATTCGGCTTT  AGAGTAACAA  ACTGTCAGTG  CTGAATTTAA
AATAACGTGA  GATTA↘AGGGT GAGTGAAGAT  AAAAAGTTTA  ATGTTTTGGT
 16S↑                        *                           200
TTCTTGGGTG  GGGTAATATA  AAAAGTATAT  TGGGCTCATG  CCCCAATCGC
 tRNA
GGAAGGCTGC  GATTCCTTTC  CTCTGCCTTC  GGCTAGGTTT  TGGCTTAGTC
AACAGTGATG  CGTAGATGTA  TATCTTTGGC  GGGGTTTTTA  CTACTCCCCC
                   *                      *              300
CTTATCCCTC  CGGTGAAGGC  GGGGCAAAAT  AAAAAGTCTG  GTGTCTATTT
 **                                                  ** *
CTTTAGCATG  GTTATTGAGT  AAGGAGAGCG  TCGGACTTGG  TCGTTCATGG
                   *               *                     400
GAACGTGTGG  GTGTCTTCGT  AAGAAACGTT  TCTGGGATAG  TTGGTAGGTG
GTAGTTTGGT  TCTGGTTACC  TAGCTTGGGT  AAAACATGGT  CAATTAACAC
            Pyso NcR                                     500
ATGGTAGTTA  AGGGCGAGAA  TGAGTATGAG  TTGGCTTTTC  TACAAGGGGG
                                         ↑ 12S
GCCACGGAGC  CCCTGAAGG   AAGCTCATGA  CCAACAATCA  GAAAAAATTC
                                                         600
```

*Nucleotide base substitution loci

FIG. 4(B)2

```
GAGGACTGTT  AGTAGACGAT  CCATACCTCC  AGTGAAAAGG  TCTTGGCGAT
                                                          700
GTGCGGGCAGC TAGACCGGGA  TATCGTTAGA  CAGGGGAGTC  CAACCAGGTG

CCAGCAGTCG  CGGTTAAACC  TGAGTTACCC  AATTCAAGTG  TGACAGTGCA
Pyso 12SAR →                                              800
AAAGGTGGTG  ACACAGCCCT  CCCCTGCTAC  GAGCGGGGGA  CAATCTTAGG AAAAAGAGAG  GATCGATCCG  GGAAGGATAA  GGGTGCAATC  TGGTTAACCC
                                                          900
TCCTGAGGAA  AGGGGAAATT  TCTTCTCTAG  GCTGAGGCCA  CGGAACCGGT GAACCGAAGA  CATGGATTTG  AGACCCATTT  ATTGCCGACG  CAAACTTTGC
                                                          1000
TTTGGGGCAG  CTGCTTGGGT  ACTACGAGCG  TGTGCTTAAA  ACTCAAAGAA CTTGGCGGCT  CGTTAACTAC  CTAGGGGAAT  ATGCGCCTTA  ATCCGATGAT
                                                          1100
CCGCGTAGCA  TCTTACTGTA  CCTTGAAAAA  GAACAGCCGG  TGTATTGCCG TCGTCAGCCT  GTTGTTCCAG  CAAAGAGAAA  CAGGCCCAAT  GGAACTGGCG
                                                          1200
ATTTGTCGAC  AGGATCCGTA  AAGTCAGGTC  GAAATACTGC  CCATGGTACG AGGGAGTGGG  TATTACAATT  CAATTTTCGA  ACTACGGAGC  TTGGAAGAAC
                                                          1300
TGTGAAATCT  CCAGGTGAAG  GTGGACTTAG  GAGTAAGGGG  AGATTAATAT GCTTCCCTGA  ACATGAATCT  AACTTGTGTA  CACATCGCCC  GTCGCTCT
                                                   ← Pyso 12SBR
```

METHOD FOR ANALYZING PHYLETIC LINEAGE OF SCALLOP

BACKGROUND OF INVENTION

1. Field of the Invention

The present invention relates to a method for analyzing the phyletic lineage of scallop, and particularly to a method for analyzing such lineage by sequencing a non-coding region found in the nucleotide base sequence of scallop's mitochondrial DNA (mtDNA).

2. Description of Prior Art

In the past, scallops have been caught and produced directly from the natural fishing grounds, but the recent increasing demands have led to artificial culturing of scallops for mass production. As a consequence thereof, certain artificial techniques have gone on to control the seeding nursery of seed scallops, which however raises a negative aspect to adversely affect the genetic structure of whole organisms, not to mention the scallops. Such artificial seeding and culture control will result in decreasing the pools of genes and diminishing the variety of phyletic lineages of scallops. This means that, in the near future, a population of particular scallops will reduce its variety of lineages and will not adapt themselves to variable changes in the surrounding circumstances to leave their offsprings, causing unexpected grave consequences. Hence, it is now required that the specific genetic structure of scallops be analyzed to determine their DNA polymorphism or hypervariable nucleotide sequence regions which are key factors to save varied lineages of scallops.

In particular, the Japanese scallops (*Patinopecten yessoensis*, which widely inhabit the cold coasts of the northern islands of Japan, the northern part of the Korean Peninsula, Sakhalin and the Kuril islands, are one of the most attractive scallops for food products and food processing. To retain the widest possible phyletic lineages of such Japanese scallops is also greatly required in view of the above-discussed artificially culturing problems.

Conventional methods for analyzing the genetic structure of one scallop population has been based on the use of isozymes or allozymes. But, such enzyme method has been found poor in sensitivity and insufficient as a tool to specifically determine and classify the lineage of each Japanese scallop population in a particular local marine area of Japan. Further, the problem of that conventional method is that it requires a great amount of samples to be analyzed, and time-consuming, inefficient steps of analyzing procedures.

In addition, there has been no report which completely analyzes the genetic characteristics of each different Japanese scallop population as well as the specific base sequence of mtDNA of the Japanese scallop. Thus, no data has been made available, which is necessary to keep the lineage of the Japanese scallops.

SUMMARY OF THE INVENTION

In view of the above-stated shortcomings, it is a primary purpose of the present invention to provide a method which assures to analyze a phyletic lineage of scallop with high precision and reliability.

For that purpose, a method in accordance with the present invention basically comprises the steps of sequencing a mitochondrial DNA (mtDNA) of the scallop to determine a nucleotide base sequence of the mtDNA, wherein the nucleotide base sequence includes a non-coding region containing a nucleotide base substitution locus which shows a sequence polymorphism indicative of a particular lineage of the scallop.

In one aspect of the present invention, the method may comprise the steps of: extracting a total DNA as a template DNA from an adductor muscle of the scallop; amplifying mtDNA from the template DNA under polymerase chain reaction, using a suitable primer set designed on the basis of nucleotide base sequences conserved among known shellfish mitochondrial 16S rRNA genes and 12S rRNA genes; sequencing the thus-amplified mtDNA while determining a non-coding region therein; thereafter, sequencing the non-coding region, using suitable primers designed on the basis of the determined nucleotide base sequences of the mtDNA; and locating a nucleotide sequence substitution locus in the non-coding region, thereby determining a particular lineage of the scallop.

Japanese scallop, *Patinopecten yessoensis*, is analyzed as to the nucleotide base sequence of mitochondrial DNA thereof, with the afore-said suitable primer set comprising Pyso 16S BF primer (5'-CGGCGMGCCAGGTCAGTTTCTATC-3') (SEQ ID NO: 3) and Pyso 12S BR primer (5'-AGAGCGACGGGCGATGTGTACAC-3'), (SE ID NO:8) while locating a non-coding region in the base sequence, and then, the non-coding region of the mtDNA is sequenced, with the afore-said suitable primers comprising Pyso 16S BF primer (5'-CGGCGMGCCAGGTCAGTTTCTATC-3') (SEQ ID NO:3), Pyso NcR primer (5'-AGGTAACCAGAACCAAACTACC-3') (SEQ ID NO:10) and Pyso 12S AR primer (5'-ACTGCTGGCACCTGGTTGGA-3') (SEQ ID NO:6).

In another aspect of the present invention, plural different amplified mtDNAs of different scallop samples, obtained by the foregoing polymerase chain reaction using the afore-said suitable primer set, may be grouped into different groups each corresponding to respective different scallop populations, and each of those amplified mtDNAs is sequenced while determining a non-coding region therein. Then, the non-coding region is sequenced, using the afore-said suitable primers, so that a nucleotide sequence substitution locus is located in the non-coding region with respect to each of the different groups, thereby determining sequence polymorphism in each of the groups, the sequence polymorphism being indicative of a particular lineage of each of the scallop, so as to classify the different scallops into particular lineages. In those steps, there may be included the steps of: comparing the nucleotide base sequence substitution loci of the different scallop samples with one another; selecting particular scallop samples from the different scallop samples, which particular samples are identical in nucleotide base sequence substitution loci to one another; obtaining a high population frequency among such particular samples; and determining identity of ancestor among the particular samples on the basis of the high population frequency so as to find identical ancestors among the different scallop populations.

In still another aspect of the invention, for high efficient analysis of plural scallop samples, after the amplification of mtDNAs of plural scallop samples, the non-coding regions of the mtDNAs may be directly sequenced, using the Pyso 16S BF, Pyso NcR and Pyso 12S AR primers, to locate nucleotide sequence substitution loci in the non-coding regions for quick analysis of lineage of each of the plural scallop samples on the different scallop population basis.

Another various advantages and features of the present invention will become apparent from reading of the descriptions hereinafter, with reference to the annexed drawings.

BRIEF DESCRIPTION OF THE DRAWINGS

FIG. 1 is a table listing all primers (SEQ ID NOs:1–10) used for amplification and sequencing of relevant DNA regions of scallops;

FIG. 2 is a table showing sequence polymorphism of non-coding regions of Japanese scallop mitochondrial DNA in each of SAROMA and AOMORI populations;

FIGS. 4(B)1 and 4(B)2 are diagrams showing base sequence codes of the whole nucleotide base sequence of (SEQ ID NO:1) mitochondrial DNA shown in the FIG. 4(A).

DETAILED DESCRIPTION OF PREFERRED EMBODIMENT OF THE INVENTION

Figure 3:
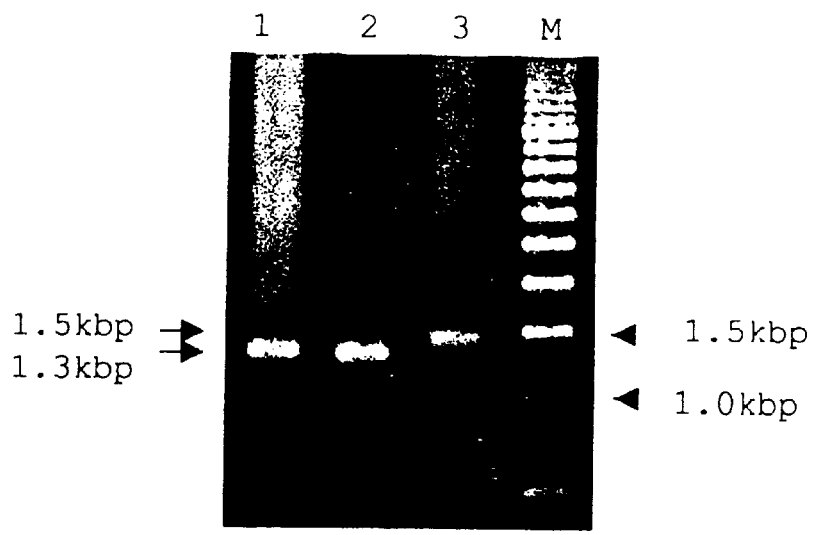
FIG. 3 is a photograph showing an electrophoresed pattern of amplified mitochondrial DNA in each of SAROMA, AOMORI and U.S. scallop samples that have undergone LA-PCR amplification.

As far as mitochondrial DNAs in vertebrates and molluscs are concerned, their complete nucleotide base sequences have been determined in some cases of species (as reported for example from Hoffmann et al., Genetics 131:397–412, 1992 and Hatzoglou et al., Genetics 140:1353–1366, 1995). The vertebrate mitochondrial DNA (mtDNA) is reported to include non-coding regions in the genomic structure thereof, which shows a great diversity of nucleotide bases, i.e. hypervariable base sequence, indicative of certain mutation occurring therein (Wilding et al., J Mol Evol 48:348–359, 1999 and Kurabayashi et al., Mol Biol Evol 17:266–277, 2000). Hence, the non-coding regions have been accepted as a criteria for lineage analysis and phylogenetic studies as well as population genetic studies. Also, the mtDNA is maternally inherited and known to exhibit a high mutation rate in vertebrates.

With regard to scallops, Sellos et al report that a 5.5 kbp mtDNA segment from a scallop (Pecten maximus) has been cloned and sequenced to find that such mtDNA segment contains the genes for two polypeptides, two rRNAs and 5 tRNAs, and intergenic sequences 8 to 125 bp in length (Genbank Accession No.X92688, 1997). But, no further studies were made by them. La Roche et al and Rigaa et al have characterized a repeat element in the mtDNA of the scallops, Placopecten magellanicus and Pecten miximus. (Mol Biol Evol 7:45–64, 1990 and J Mol Evol 41:189–195, 1995) According to Fuller and Zouros, 1993, such repeat element is found to be responsible for the inter-and intraindividual length variation of mtDNA in the scallop, Placopecten magellanicus (Curr Genet 23:365–369, 1993).

In view of the foregoing prior findings about the mtDNA of non-Japanese scallop species, we, the inventors, have made a specific analysis to determine the nucleotide base sequence in the mtDNA of the Japanese scallop (Patinopecten yessoensis) and found that the sequence of mtDNA fragment from such Japanese scallop contains a non-coding region which shows sequence polymorphism in each of different scallop populations.

Hereinafter, a detailed description will be made of one preferred example of processes which we effected for analyzing the Japanese scallop's mtDNAs in two typical different populations along with a comparative analysis with a foreign scallop and for determining detailed phyletic lineage of each Japanese scallop population.

1. DNA Extraction

In the present example, the following three different kinds of scallops were provided: two different Japanese scallops, one being cultured in the Lake Saroma, Hokkaido, Japan, inclusive of plural individuals in the same scallop population (hereinafter, "SAROMA") and another being cultured in the seaboard of Aomori, Japan, inclusive of plural individuals in the same scallop population (hereinafter, "AOMORI" , and foreign scallops (Agropecten irradians) cultured in the North America (hereinafter, "US Sample"). It is noted that the description of this section will be dedicated only to one sample of individual taken from each scallop individual of the SAROMA and AOMORI populations as well as one US Sample, for the sake of simplicity.

Approx. 50–100 mg of small pieces of adductor muscle of each of the afore-said three different samples was prepared, so that three scallop samples of about 50–100 mg are provided for the DNA extraction steps to be set forth below.

To each of those three samples was added 500 $\mu$ l of TNES-Urea buffer solution containing 20 mg/ml of proteinase K, and then, the samples were incubated at 37° C. for 2 hours. After the incubation, the lysate was extracted twice with phenol-chloroform-isoamyl alcohol (25:24:1) (the so-called "phenol-chloroform treatment", after which, a whole DNA was recovered by ethanol precipitation and dissolved in 50 $\mu$ l of distilled water. This DNA extraction was done on the basis of procedures made by Asahida et al. (as disclosed from Fisheries Sci 62:727–730, 1996). For plural samples to be treated under this process, the DNAs were recovered form the lysate after the incubation, using the Multiscreen 96-well Filtration Plates FB (Millipore) and purified by isopropanol precipitation, using the 96-well DNA Precipitation HL Kit (Edge Bio Systems)

2. Amplification of mtDNA Fragment

In order to amplify a target mtDNA from each of the thus-extracted total DNAs (template DNAs), a long and accurate polymerase chain reaction (hereinafter, LA-PCR) was employed, (the LA-PCR kit is available from Takara Shuzo), and primers to be used in the LA-PCR are designed, as listed in FIG. 1, on the basis of nucleotide sequences conserved among the known shellfish mitochondrial 16S rRNA genes and 12S rRNA genes. Specifically, at first, 50 $\mu$ l of reaction solution was prepared by mixing approx. 5–10 ng of the template DNA with the under-listed materials.

LA-Tag polymerase: 5 units, LA-PCR buffer: 1x, $MgCl_2$:2.5 mM dNTP: each at 400 $\mu$ M , primers: each at 0.2 $\mu$ M The LA-PCR was performed in the foregoing reaction solution, using several combinations of the following eight primers: Pyso 16S AF, Pyso 16S AR, Pyso 16S BF, Pyso 16S BR, Pyso 12S AF, Pyso 12S AR, Pyso 12S BF and Pyso 12S BR. The base sequences of those primers are listed in FIG. 1. The steps of LA-PCR consist of effecting an initial denaturation at 94° C. for 7 minutes and then conducting 35 cycles of the following series of reactions: denaturation at 98° C. for 20 seconds, annealing at 55° C. for 1 minute and extension at 72° C. for 10 minutes.

The PCR products were electrophoresed through a 0.7% agarose gel and visualized by ethidium bromide staining. After the electrophoresis, the amplified DNAs were excised from the gel and purified by the GFX PCR DNA and Gel Band Purification Kits (Ameraham). Then, the thus-treated amplified DNAs were cloned by E. coli XL1-1 Blue, using a vector of pGEM-T Easy (Promega). The nucleotide base sequence of each of the amplified DNA fragments was determined by means of a dye-terminator method (e.g. by the BigDye Terminator Cycle Sequencing Kit produced by PE Biosystems), using T7 primer, SP6 primer or suitable primers selected from the primers listed in FIG. 1. Alternatively, the amplified DNA fragments, after the purification as above, may be directly sequenced without the foregoing cloning by means of the dye-terminator method.

Figure 4A:
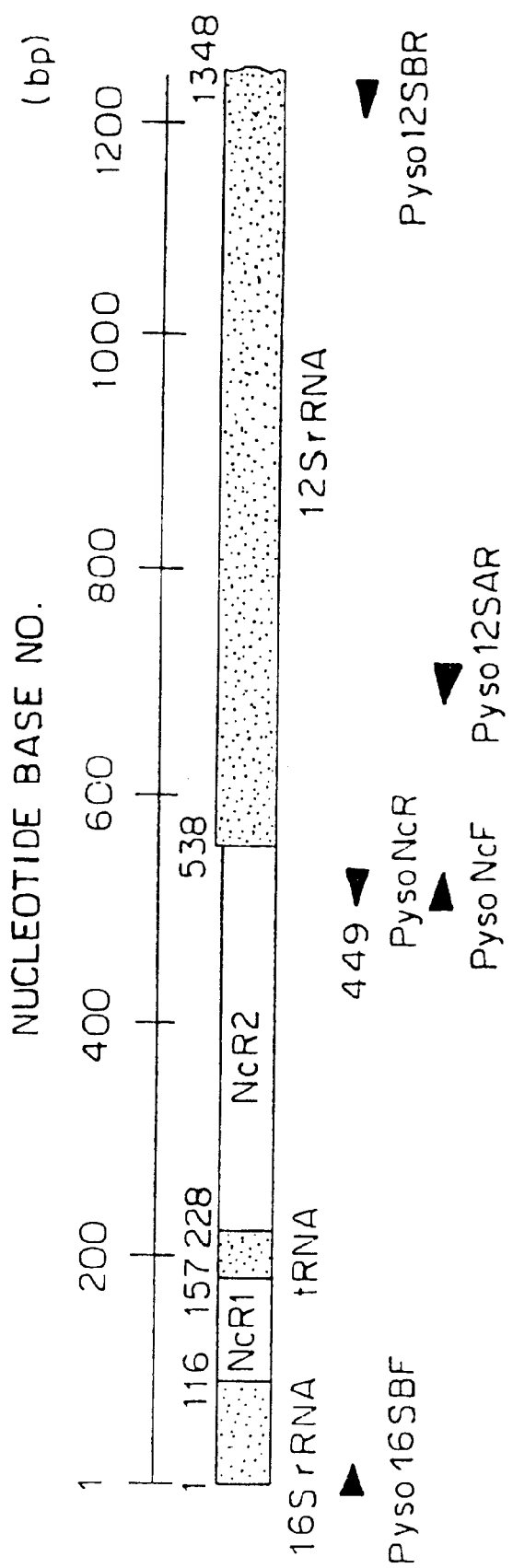
FIG. 4(A) is a diagram which schematically shows the nucleotide base sequence (SEQ ID NO:1) of mitochondrial DNA common to the SAROMA and AOMORI samples.

The amplified DNA fragments was visualized in such elecrophoresed patterns as shown in FIG. 3, wherein it is observed that both SAROMA and AOMORI samples show their respective distinctive bands at 1.3 kbp level, whereas the US sample shows its distinctive band at 1.5 kbp level, with respect to the marker reference bands (M) in the gel medium. This base-pair difference obviously indicates that the Japanese scallops are different in the structure of mitochondria from the US scallop. Also, the experiment shows that those two scallops can be easily differentiated from each other by the PCR in terms of species and habitat. Moreover, this result leads us to confirm that the 1.3 kbp bands of both two Japanese samples are detected by the primer set: Pyso 16S BF and Pyso 12S BR, whereas the 1 .5 kbp band of US sample is detected by the primer set: Pyso 12S BF and Pyso 16S BR. The 1.3 kbp DNA from the SAROMA and AOMORI samples were subjected to sequencing, using a suitable sequencer. Consequently, the 1.3 kbp band of the SAROMA sample is found identical in base sequence to that of the AOMORI sample, excepting only two bases. The resulting data of nucleotide base sequences for those two samples were analyzed by homology search, using NCBI BLAST server or tRNAscan-SE Search Server (www.genetics.wustl.edu/eddy/tRNAscan-SE). As a result of this analysis, the base sequences of both two Japanese samples are found to contain the following three particular genes: 16S rRNA gene, tRNA gene and 12S rRNA gene, and further contain the following first and second non-coding regions: NcR1 and NcR2. (see FIGS. 4(A), 4(B)1 and 4(B)2) We also found that the 16S rRNA and 12S rRNA gene regions each shows the highest homology to the respective 16S rRNA and 12S rRNA gene regions of the mtDNA of the scallop, Pecten maximus, (sequenced by Sellos et al., 1997) and come to the conclusion that the 1.3 kbp DNA in question is derived from mitochondrial DNA, not a nuclear DNA. That is, the 1.3 kbp DNA is now determined to be a mtDNA of the Japanese scallops (*Patinopecten yessoensis*), the schematic base sequence of which is shown in FIG. 4(A). Reference is also made to FIGS. 4(B)1 and 4(B)2 which specifically depict a whole encoded nucleotide base sequence of the 1.3 kbp mtDNA of Japanese scallop.

Based on the sequence determination of 1.3 kbp mtDNA from some individuals, we determined that the non-coding regions NcR 1 and NcR2 appear to intensively show sequence variation and a high rate of mutation. Those two non-coding regions NcR1, NcR2 are considered to be the regions where specific base substitution or mutation occurs among individuals of the Saroma and Aomori scallop populations.

3. Analysis of the Non-coding Regions of mtDNA

In view of mtDNA being maternally inherited and having a high mutation rate, the mtDNAs of Japanese scallops, particularly the non-coding regions (NcR1 and NcR2) therein, are also maternally inherited and considered to have high mutation rate as suggested above. Thus, such non-coding regions were analyzed as to the base sequence thereof, by taking total 19 samples of 1.3 kbp mtDNA fragments of SAROMA scallops (i.e. 19 scallop individuals of the SAROMA population) and by taking total 20 samples of 1.3 kbp mtDNA fragments of AOMORI scallops (i.e. 20 scallop individuals of the AOMORI population). Of course, those plural samples were already subjected to the above-described all treatments and processes including the LA-PCR, with appropriate grouping of the amplified 1.3 kbp mtDNA fragments into different groups with suitable corresponding labels, and then subjected to sequencing under the same conditions as described above.

The non-coding regions (NcR1 and NcR2) found in the mtDNA for each sample may be sequenced by any suitable method. In the present example, the aforementioned dye-terminator method was conducted, using the three primers: Pyso 16S BF, Pyso NcR and Pyso 12S AR, to determine specific nucleotide base sequence of the non-coding regions for each sample of the SAROMA (19 samples) and AOMORI (20 samples). Alternatively, in place of the dye-terminator method, a denaturing gradient gel electrophoresis may be employed, using any suitable primer set, for that purpose.

Finally, upon determination of base sequence of the non-coding regions for each of the SAROMA and AOMORI samples, it is revealed that plural different nucleotide base substitution loci are located in the non-coding regions (particularly in the second non-coding region NcR2), as shown in FIGS. 2, 4(B)1 and 4(B)2, which indicates sequence polymorphism in the mtDNA among the scallop individuals. From the FIG. 2, it is seen that the SAROMA population includes 10 different matrilineages (Gs-1 to Gs-10) classified therein, whereas on the other hand, the AOMORI population includes 5 different matrilineages (Ga-1 to Ga-5) classified therein.

The results of the above analysis further show that the haplotypes Gs-1 and Gs-8 of SAROMA population correspond in both nucleotide base sequence and sequence substitution loci to the haplotypes Ga-1 and Ga-4 of AOMORI population, respectively, within the range of nucleotide base sequence Nos. 126 to 378 as in FIG. 2, and suggest that total of matrilineal population frequencies for each of those haplotypes of SAROMA and AOMORI can amount to as high as 42.11 and 80%, respectively. This high population frequency of the common haplotypes in both populations suggests that the two SAROMA's haplotypes Gs-1, Gs-8, which correspond to the two AOMORI's haplotypes Ga-1, Ga-4, respectively, are matrilineal ancestors in the Japanese scallop population. In this respect, one can however infer from this result that there would be some artificial migration from the SAROMA population to the AOMORI population, or vice versa, but such assumption is less realistic in view of the data of FIG. 2 showing the variety of scallop individuals specific to each of the SAROMA and AOMORI populations.

Additionally, from the results of this analysis, with regard to the sequence Nos. 229 through 449, we calculated 0.80% nucleotide base diversity for the SAROMA population and 0.38% nucleotide base diversity for the AOMORI population. Namely, the nucleotide base diversity of SAROMA population is found about twice that of AOMORI population, which shows that the former have a greater pool of genes relative to that of the latter.

From the descriptions made thus far, in accordance with the present invention, it is to be appreciated that:

(i) The mtDNA of the Japanese scallops is analyzed as to its nucleotide base sequence by means of PCR. The nucleotide base sequence is encoded as shown in FIGS. 4(B)1 and 4(B)2. The non-coding regions of the mtDNA, which show sequence polymorphism, are further sequenced to locate nucleotide base substitution loci therein, thereby comparatively determining a population frequency in each scallop individual of a particular scallop population and finding identical nucleotide base sequences among different scallop populations. Based on those population frequency and identical nucleotide base sequences, it is easily possible to classify the individuals of each scallop population into different lineages, and also, determination of the identical nucleotide base sequences among different scallop populations results in ascertaining that some of them belong to a materilineally homogenous population. Accordingly, it is possible with such analysis to elucidate the phyletic lineages of scallops and classify the scallops into different lineages, and (ii) In contrast to the conventional enzyme analysis method, the combination of PCR and dye-terminator methods in the present invention, not merely provides a highly improved sensitivity and precision in analyzing the mtDNA of scallop, but also provides a rapid analyzing process therefor, since it does not require a great amount of samples and any other complicated steps as found in the enzyme method. Many samples can also be analyzed with high precision and rapidity.

In the above-described analysis, we, the inventors, find it necessary to make a comparative search for genomic structure between the natural scallop population and artificially cultured scallop population on the regional basis.

While having described the present invention, it should be understood that the invention is not limited to the illustrated examples and embodiments, but any other modifications, replacements and additions may be applied thereto without departing from the scopes of appended claims. Basically, the processes described above in the present invention may also be applied to other kinds of scallops than the Japanese scallops, with some adjustments in designing primers to be used, PCR conditions and so forth, for the purpose of phyletic lineage analysis.

What is claimed is:

1. A method for determining lineage of scallop, comprising:
   extracting DNA from an adductor muscle of a scallop to serve as a template DNA;
   amplifying mitochondrial DNA from said template DNA by polymerase chain reaction, using a first primer set designed on the basis of nucleotides conserved in shellfish mitochondrial 16S rRNA genes and a second primer set designed on the basis of nucleotides conserved in shellfish mitochondrial 12S rRNA genes;
   sequencing the amplified mitochondrial DNA to obtain a nucleotide base sequence a said mitochondrial DNA;
   determining at least one non-coding region in said nucleotide base sequence;
   sequencing said at least one non-coding region, using a third primer set designed on the basis of said nucleotide base sequence of said amplified mitochondrial DNA;
   identifying sequence polymorphism at nucleotide base substitution loci in said non-coding region; and
   determining the lineage of said scallop from the sequence polymorphism identified at nucleotide base substitution loci in said non-coding region.

2. The method according to claim 1, wherein said amplified mitochondrial DNA is directly sequenced by a dye-terminator method, without being cloned.

3. The method according to claim 1, wherein said amplified mitochondrial DNA and said at least one non-coding region are both sequenced by a dye-terminator method.

4. The method according to claim 1, wherein said extracting step extracts DNA from a plurality of different scallops from different species, said amplifying step amplifies the mitochondrial DNA from each different species of scallop of said plurality of different scallops by said polymerase chain reaction, using said first and second primer sets, and, then directly sequencing the non-coding regions of the mitochondrial DNA from each different species of scallop, without being cloned, by a dye-terminator method using said third primer set, thereby identifying different nucleotide base substitution loci in said non-coding regions of the mitochondrial DNA from different species of scallops.

5. The method according to claim 1, wherein said scallop is Japanese scallop, *Patinopecten yessoensis*, wherein said first primer set comprises Pyso 16S BE primer (SEQ ID NO:3) and said second primer set comprises Pyso 12S BR primer (SEQ ID NO:8), and wherein said third primer set comprises Pyso 16S BF primer (SEQ ID NO:3), Pyso NcR primer (SEQ ID NO:10) and Pyso 12S AR primer (SEQ ID NO:6).

6. The method according to claim 1, wherein said scallop is Japanese scallop, *Patinopecten yessoensis*, said first primer set comprises Pyso 16S BF primer (SEQ ID NO:3), said second primer set comprises Pyso 12S BR primer (SEQ ID NO:8), and said third primer set comprises Pyso 16S BF primer (SEQ ID NO:3), Pyso NcR primer (SEQ ID NO:10) and Pyso 12S AR primer (SEQ ID NO:6), wherein a plurality of Japanese scallops, which are grouped into at least one scallop population, are provided, and wherein:

at said step of amplifying mitochondrial DNA, the mitochondrial DNA of said at least one scallop population is amplified, using said first and second primer sets, whereby about 1.3 kbp mitochondrial DNA is determined in each of said at least one scallop population;

at said step of sequencing the amplified mitochondrial DNA, a nucleotide base sequence of said about 1.3 kpb mitochondrial DNA is determined;

at said step of determining said at least one non-coding region, two non-coding regions are determined in said nucleotide base sequence; and at said step of sequencing said at least one non-coding region, said two non-coding regions are sequenced, using said third primer set, so that nucleotide base substitution loci are located in said two non-coding regions with regard to each of said at least one scallop population, thereby identifying sequence polymorphism therefrom and, on the basis of said sequence polymorphism, determining the particular lineages of said plurality of Japanese scallops in said at least one scallop population.

7. The method according to claim 6, wherein said at least one scallop population comprises one population of scallops inhabiting Lake Saroma, Hokkaido, Japan and another population of scallops inhabiting a seacoast of Aomori, Japan.

8. The method according to claim 6, wherein said nucleotide base sequence of the about 1.3 kbp mitochondrial DNA is SEQ ID NO:11.

9. A method for determining lineages of a plurality of scallops, comprising:

providing different scallop samples collected from different populations of said plurality of scallops;

extracting DNAs from adductor muscles of said different scallop samples to serve as template DNAs;

amplifying mitochondrial DNA fragments from each of said template DNAs by polymerase chain reaction, using a first primer set designed on the basis of nucleotides conserved in shellfish mitochondrial 16S rRNA genes and a second primer set designed on the basis of nucleotides conserved in shellfish mitochondrial 12S rRNA genes;

grouping the amplified mitochondrial DNA fragments for said different scallop samples to thereby provide different groups, each corresponding to a scallop population among said different scallop populations;

sequencing said amplified mitochondrial DNA fragments per each of said different groups to obtain a nucleotide base sequence for each of said different groups;

determining at least one non-coding region;

sequencing said at least one non-coding region, using a third primer set designed on the basis of at least one nucleotide base sequence of said amplified mitochondrial DNA fragments from said different groups;

locating nucleotide base substitution loci in said at least one non-coding region with regard to each of said different groups; and identifying sequence polymorphism from said nucleotide base substitution loci in each of said different groups and classifying said different scallop samples according to the identified sequence polymorphism to thereby determine the lineage of said scallop in each of said different scallop populations.

10. The method according to claim 9, wherein said amplified mitochondrial DNA fragments and said at least one non-coding region are both sequenced by means of a dye-terminator method.

11. The method according to claim 9, which further comprises:

comparing the nucleotide base substitution loci of said different scallop samples with one another;

selecting particular scallop samples from said different scallop samples;

obtaining a population frequency among said particular scallop samples; and identifying ancestors among said particular samples on the basis of said population frequency and finding identical ancestors among said different scallop populations to classify scallops into different lineages.

* * * * *

SEQUENCE LISTING

<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: Pyso 16S AF primer

<400> SEQUENCE: 1
gcaccttttg catcatggct tat                                              23

<210> SEQ ID NO 2
<211> LENGTH: 23
<212> TYPE: DNA
<213> ORGANISM: Artificial Sequence
<220> FEATURE:
<223> OTHER INFORMATION: Pyso 16S AR primer

<400> SEQUENCE: 2
ataagccatg atgcaaaagc tgc                                              23

<210> SEQ ID NO 3
<211> LENGTH: 25
<212> TYPE: DNA
<213> ORGANISM: Artificial Sequence
<220> FEATURE:
<223> OTHER INFORMATION: Pyso 16S BF primer

<400> SEQUENCE: 3
cggcgaagcc aggtcagttt ctatc                                            25

<210> SEQ ID NO 4
<211> LENGTH: 26
<212> TYPE: DNA
<213> ORGANISM: Artificial Sequence
<220> FEATURE:
<223> OTHER INFORMATION: Pyso 16S BR primer

<400> SEQUENCE: 4
aaactgacct ggcttacgcc ggtctg                                           26

<210> SEQ ID NO 5
<211> LENGTH: 20

-continued

```
<212> TYPE: DNA
<213> ORGANISM: Artificial Sequence
<220> FEATURE:
<223> OTHER INFORMATION: Pyso 12S AF primer

<400> SEQUENCE: 5
tccaaccagg tgccagcagt                                              20

<210> SEQ ID NO 6
<211> LENGTH: 20
<212> TYPE: DNA
<213> ORGANISM: Artificial Sequence
<220> FEATURE:
<223> OTHER INFORMATION: Pyso 12S AR primer

<400> SEQUENCE: 6
actgctggca cctggttgga                                              20

<210> SEQ ID NO 7
<211> LENGTH: 23
<212> TYPE: DNA
<213> ORGANISM: Artificial Sequence
<220> FEATURE:
<223> OTHER INFORMATION: Pyso 12S BF primer

<400> SEQUENCE: 7
gtgtacacat cgcccgtcgc tct                                          23

<210> SEQ ID NO 8
<211> LENGTH: 23
<212> TYPE: DNA
<213> ORGANISM: Artificial Sequence
<220> FEATURE:
<223> OTHER INFORMATION: Pyso 12S BR primer

<400> SEQUENCE: 8
agagcgacgg gcgatgtgta cac                                          23

<210> SEQ ID NO 9
<211> LENGTH: 22
<212> TYPE: DNA
<213> ORGANISM: Artificial Sequence
<220> FEATURE:
<223> OTHER INFORMATION: Pyso NcF primer

<400> SEQUENCE: 9
ggtagtttgg ttctggttac ct                                           22

<210> SEQ ID NO 10
<211> LENGTH: 22
<212> TYPE: DNA
<213> ORGANISM: Artificial Sequence
<220> FEATURE:
<223> OTHER INFORMATION: Pyso NcR primer

<400> SEQUENCE: 10
aggtaaccag aaccaaacta cc                                           22

<210> SEQ ID NO 11
<211> LENGTH: 1348
<212> TYPE: DNA
<213> ORGANISM: Patinopecten yessoensis

<400> SEQUENCE: 11
gaagccaggt cagtttctat cttctttcat taaaatttag gcggtagggt acgaaaggac  60
```

-continued

| | | | | | |
|---|---|---|---|---|---|
| attcggcttt | agagtaacaa | actgtcagtg | ctgaatttaa | aataacgtga | gattaagggt | 120 |
| gagtgaagat | aaaaagttta | atgttttggt | ttcttgggtg | gggtaatata | aaaagtatat | 180 |
| tgggctcatg | ccccaatcgc | ggaaggctgc | gattcctttc | ctctgccttc | ggctaggttt | 240 |
| tggcttagtc | aacagtgatg | cgtagatgta | tatctttggc | ggggttttta | ctactccccc | 300 |
| cttatccctc | cggtgaaggc | ggggcaaaat | aaaaagtctg | gtgtctattt | ctttagcatg | 360 |
| gttattgagt | aaggagagcg | tcggacttgg | tcgttcatgg | gaacgtgtgg | gtgtcttcgt | 420 |
| aagaaacgtt | tctgggatag | ttggtaggtg | gtagtttggt | tctggttacc | tagcttgggt | 480 |
| aaaacatggt | caattaacac | atggtagtta | aggcgcagaa | tgagtatgag | ttggcttttc | 540 |
| tacaagggg | gccacggagc | cccttgaagg | aagctcatga | ccaacaatca | gaaaaaattc | 600 |
| gaggactgtt | agtagacgat | ccatacctcc | agtgaaaagg | tcttggcgat | gtgcggcagc | 660 |
| tagaccggga | tatcgttaga | cagggagtc | caaccaggtg | ccagcagtcg | cggttaaacc | 720 |
| tgagttaccc | aattcaagtg | tgacagtgca | aaggtggtg | acacagccct | cccctgctac | 780 |
| gagcggggga | caatcttagg | aaaaagagag | gatcgatccg | ggaaggataa | gggtgcaatc | 840 |
| tggttaaccc | tcctgaggaa | aggggaaatt | tcttctctag | gctgaggcca | cggaaccggt | 900 |
| gaaccgaaga | catggatttg | agacccattt | attgccgacg | caaactttgc | tttggggcag | 960 |
| ctgcttgggt | actacgagcg | tgtgcttaaa | actcaaagaa | cttggcggct | cgttaactac | 1020 |
| ctagggaat | atgcgcctta | atccgatgat | ccgcgtagca | tcttactgta | ccttgaaaaa | 1080 |
| gaacagccgg | tgtattgccg | tcgtcagcct | gttgttcgag | caaagagaaa | caggcccaat | 1140 |
| ggaactggcg | atttgtcgac | aggatccgta | aagtcaggtc | gaaatactgc | ccatggtacg | 1200 |
| agggagtggg | tattacaatt | caattttcga | actacggagc | ttggaagaac | tgtgaaatct | 1260 |
| ccaggtgaag | gtggacttag | gagtaagggg | agattaatat | gcttccctga | acatgaatct | 1320 |
| aacttgtgta | cacatcgccc | gtcgctct | | | | 1348 |